United States Patent
Cincotta et al.

(10) Patent No.: US 6,706,674 B2
(45) Date of Patent: Mar. 16, 2004

(54) NONAQUEOUS HAIR STYLING COMPOSITION AND METHOD OF USE

(75) Inventors: Joseph J. Cincotta, Trumbull, CT (US); Linda Coppola, Trumbull, CT (US)

(73) Assignee: The Andrew Jergens Company, Cincinnati, OH (US)

( * ) Notice: Subject to any disclaimer, the term of this patent is extended or adjusted under 35 U.S.C. 154(b) by 427 days.

(21) Appl. No.: 09/764,942

(22) Filed: Jan. 17, 2001

(65) Prior Publication Data

US 2002/0155962 A1 Oct. 24, 2002

(51) Int. Cl.[7] .............................. C11D 3/37; C11D 3/44; A61K 7/09; A61K 7/11
(52) U.S. Cl. ................ 510/119; 510/122; 510/128; 510/434; 510/476; 510/477; 424/70.2; 424/70.15; 424/70.16; 424/401; 8/127.51
(58) Field of Search .................. 510/119, 122, 510/128, 434, 476, 477; 424/70.2, 70.15, 70.16, 401; 8/127.51

(56) References Cited

U.S. PATENT DOCUMENTS

| | | | |
|---|---|---|---|
| 5,830,440 A | * | 11/1998 | Sturla et al. ................... 424/47 |
| 5,853,706 A | * | 12/1998 | Klar ........................... 424/70.1 |
| 6,524,564 B1 | * | 2/2003 | Kim et al. ............... 424/70.12 |
| 2002/0155962 A1 | * | 10/2002 | Cincotta et al. ............ 510/119 |

* cited by examiner

*Primary Examiner*—Brian P Mruk
(74) *Attorney, Agent, or Firm*—Piper Rudnick LLP; Steven B. Kelber

(57) ABSTRACT

Disclosed is a hair styling composition which includes a vinyl copolymer and a nonaqueous solvent. Another disclosed hair styling composition contains a vinyl copolymer, a nonaqueous solvent, a urethane copolymer, a polyester and optionally a second nonaqueous solvent. Film formers and other additives may be included in the composition. The compositions are applied to the hair. Heat may be used in connection with the application. A method of making the compositions by adding copolymers one at a time and stirring until clear mixtures are obtained after each addition is disclosed.

8 Claims, No Drawings

NONAQUEOUS HAIR STYLING COMPOSITION AND METHOD OF USE

FIELD OF THE INVENTION

The invention relates a nonaqueous hair styling composition for creating a temporary shape or configuration in hair. The invention also relates a method for making and using the nonaqueous hair styling composition.

BACKGROUND OF THE INVENTION

There is a widespread desire to be able to impart particular shapes or configurations to hair (human or animal) and to be able to simultaneously provide shine, manageability, body, weight and a moisture barrier to the hair.

One approach to imparting a particular shape or configuration to hair involves permanent alteration of the hair. Permanent alteration generally involves the use of chemical agents to react with the hair in order to achieve the desired alteration. Permanent alterations are time consuming procedures that involve strong chemicals along with lengthy and sometime uncomfortable procedures. Due to the use of the chemical agents, permanent alterations may result in damage to the hair and may impact the hair's texture, resilience and shine.

Another approach to imparting a particular shape or configuration to hair is accomplished through temporary alteration of the hair. Temporary alteration typically involves applying a hair styling composition to the hair that can be later removed with water and/or detergent.

Hairdressing in the past decade has undergone a transition from the heavy dependence on permanent alteration processes to the relatively simple and safe techniques of applying hair styling compositions to impart a particular temporary shape or configuration to hair.

This technique is aided by a wide variety of hair styling compositions such as hair sprays, mousses, lotions and gels that fix or hold the hair in a particular shape or configuration. These products are typically applied to wet or dampened hair and are generally not rinsed out. The hair styling composition is then combed or spread through the hair, and the hair is shaped into a desired configuration and allowed to dry. The shape or configuration that is obtained varies depending on the styling composition utilized. Alternatively, hairsprays containing high concentrations of ethyl alcohol are generally applied to styled hair after drying. They are intended to create an invisible matrix on the hair surface that imparts rigidity to the desired style and resistance to moisture and mechanical agitation.

A simple hair styling composition typically includes a film forming polymer, plasticizer, solvent, disentangling agent, softening agent, glossing agent and fragrance. The desired action of these compositions for maintaining hairstyles derives mainly from the influence of the film forming polymer(s). A thin coating comprising a polymeric film former is deposited on the hair surface and is intended to have the following effects:

1. To exert a "mechanical" effect on the individual hair fibers. Film forming polymers adhere to the hair surface creating a transparent sheath which remains on the hair after drying. This film aids in physically retaining the desired shape or configuration and slows down the return of the fiber to its natural shape by gravity or mechanical agitation.
2. The polymer makes the hair sufficiently rigid, fusing the individual hairs together at points of contact for better cohesion and resistance to deformation.
3. The film forming polymer if formulated correctly creates a moisture barrier on the surface of the hair. This temporarily protects the hair from reversion to its natural shape due to high humidity conditions.

Early hair styling compositions consisted of aqueous and hydroalcoholic gels of natural polymers such as gum tragacanth, karaya gum, gum arabic, alginates, etc. They created excessively hygroscopic, dulling films which became tacky in a humid atmosphere, causing fibers to fuse together in clumps and stick to the head. The first hairsprays were nothing more that alcohol solutions of shellac (hair lacquers). Unfortunately, while this material held the hair in place, it produced a water insoluble film that was difficult to wash out.

Today a formulating chemist can select from numerous commercially available synthetic film forming polymers with varying degrees of solubility in water and alcohol. Formulation of styling products can however still cause a dilemma to the chemist because the desired characteristics are numerous and sometimes contradictory in nature. A relatively sophisticated set of criteria which consumers desire in hair styling compositions has been developed in order to meet the consumer's demand for performance and aesthetic appeal. For example, the polymer film deposited by the hair styling composition should hold the hair in the desired style or configuration despite the weather conditions such as high humidity and wind and the rigors of agitation. In addition, the hair styling composition should leave the hair with a glossy sheen, body, sufficient weight, and softness. The hair styling composition should provide these properties without leaving the hair feeling unmanageably stiff, harsh, brittle, sticky, greasy, tacky or excessively coated. The hair styling composition should be sufficiently water soluble to be readily removed by detergents and water. The hair styling composition should deposit a transparent, colorless, continuous film, and provide the glossy sheen of natural, healthy hair. In addition, the hair styling composition should be compatible with other hair styling compositions so that it can be used for touch-up of a previously arranged hairdo.

Most hair styling compositions that are used to hold hair in place are alcoholic (almost exclusively ethanol), hydroalcoholic or aqueous based compositions containing one or more film forming polymers.

The ethanol based styling compositions have the advantage of quick dry-time. The ethanol volatilizes quickly (relative to water) leaving behind the film former. The disadvantage however lies in the dehydrating effects of ethanol containing compositions on both keratin fibers and human scalp. After several successive uses hair typically becomes quite dry in texture and dull in appearance, scalp may flake, hair loses it natural elasticity becomes brittle and typically splits or cracks. Concurrently, the cuticle layers of the keratin fibers begin to raise or lift creating frizz. Polymeric film formers exclusively soluble in ethanol and ethanol/water containing compositions typically are quite substantive to hair hindering easy removal with water and detergent and have the tendency to flake and/or lose their hold properties when combed or brushed.

Aqueous compositions suffer from inordinately long dry times and therefore can not be applied to already dried hair without causing reversion of hair to its natural configuration or shape with loss of style. Typically water soluble polymers are either quite susceptible to high humidity conditions or have weak hold properties. Typically, these hold properties are lost if treated hair is combed or brushed.

For the foregoing reasons, there exists a need for a nonaqueous hair styling composition which can provide hold to the hair while simultaneously providing shine, manageability, weight and body, frizz control, conditioning and moisturization to hair without the above mentioned disadvantages.

SUMMARY OF THE INVENTION

In accordance with the invention, an improved hair styling composition is provided which includes at least one vinyl copolymer and at least one nonaqueous solvent therefor. In a preferred embodiment, the hair styling composition includes, in addition to the vinyl copolymer at least one urethane copolymer, at least one polyester and at least one additional nonaqueous solvent therefor. Various performance enhancing additives may be provided for special purposes including film formers, viscosity controlling agents, humectants, occlusives, hair conditioning agents, sunscreens, emollients, antistatic agents, fragrances, natural oils, alaphatic hydrocarbons and silicones. A preferred hair styling composition in accordance with the invention of the type having two primary components may be one in which the components are present in the following ranges (percent by weight):

| Component | Range | Preferred Range | More Preferred Range |
|---|---|---|---|
| Vinyl Copolymer | 2.5–15 | 3.0–10 | 5–10 |
| First Nonaqueous Solvent | 40–97.5 | 45–97 | 50–95 |

A preferred hair styling composition in accordance with the invention of the type having five main components may be one in which the components are present in the following ranges percent by weight:

| Component | Range | Preferred Range | More Preferred Range |
|---|---|---|---|
| Vinyl Copolymer | 2.5–15 | 3.0–10 | 5–10 |
| First Nonaqueous Solvent | 40–97.5 | 45–97 | 50–95 |
| Urethane Copolymer | 0.1–6.0 | 0.2–4.0 | 0.2–2.0 |
| Polyester | 0.1–6.0 | 0.2–4.0 | 0.2–3.0 |
| Second Nonaqueous Solvent | 0–40 | 2.5–35 | 10.0–30 |

In either the two primary components or five primary components type of hair styling composition in accordance with the invention, they may contain the following additional performance enhancing additives or components which, if present, are present in the following ranges percent by weight:

| Component (percent by weight) | Range (percent by weight) | Preferred Range (percent by weight) | More Preferred Range (percent by weight) |
|---|---|---|---|
| Film Former | 1.0–10 | 1.5–7.5 | 2.0–5.0 |
| Viscosity Controlling Agent | 0.1–1.0 | 0.15–0.75 | 0.15–0.50 |
| Humectant | 0.2–5.0 | 0.5–3.5 | 0.5–2.0 |
| Occlusive | 0.2–5.0 | 0.5–3.5 | 0.5–2.0 |
| Hair Conditioning Agent | 0.1–2.0 | 0.1–1.5 | 0.2–1.0 |
| Sunscreen | 0.1–2.0 | 0.2–1.5 | 0.2–1.0 |
| Emollient | 0.1–5.0 | 0.1–3.0 | 0.2–3.0 |
| Antistatic Agent | 0.1–1.0 | 0.2–0.8 | 0.2–0.5 |
| Fragrance | 0.05–0.2 | 0.05–0.15 | 0.05–0.10 |

A most preferred vinyl copolymer is Vinyl caprolactam/PVP/dimethylaminoethyl methacrylate copolymer. Other preferred vinyl copolymers include PVP/VA/vinyl propionate copolymer, PVP/VA copolymer, Sodium acrylate/vinyl alcohol copolymer, Stearylvinyl ether/MA copolymer, VA/crotonates/vinyl neodecanoate copolymer, VA/crotonates/vinyl propionate copolymer, VA/isobutyl maleate/vinyl neodecanoate copolymer, VA/vinyl butyl benzoate/crotonates copolymer, and mixtures thereof.

In the hair styling composition of the invention, the preferred nonaqueous solvent comprises one or more polyhydric $C_2$–$C_6$ alcohols, which may include propylene glycol, glycerin, dipropylene glycol, butylene glycol, pentylene glycols, hexylene glycols, and C2–C6 polyhydric alcohols containing an ether linkage and mixtures thereof. A hair styling composition the invention of the type in which an additional nonaqueous solvent is employed may utilize one or more monohydric $C_2$–$C_3$ alcohols for that purpose. Such $C_2$–$C_3$ alcohol(s) may include ethanol, 1-propanol, 2-propanol and monohydric C2–C3 alcohols containing an ether linkage and mixtures thereof.

When a hair styling composition in accordance with the invention employs a urethane copolymer, it may be selected from the group consisting of urethane copolymers containing pendant hydroxyl groups, esters, silicones, triglycerides, tertiaryamines or isophorone diisocyanate functionalites. The preferred urethane copolymer is glycereth-7-diglycerol-PEG-15 cocamine/isophorene diissocynate.

In a hair styling composition in accordance with the invention that includes a polyester, it may be selected from the group consisting of adipic acid/diethylene glycol/glycerin crosspolymer, tripentanediol/adipic acid/glycerin crosspolymer, tripentanediol/adipic acid/isononanoic acid crosspolymer, tripentanediol/adipic acid copolymer, and mixtures thereof. The preferred polyester is trimethylpentanediol/adipic acid/glycerin crosspolymer.

The principles of the invention may be embodied in various kinds of hair styling compositions, including styling laminators, serums, gels, creams, fixatives, sprays and lotions.

In further accordance with the invention, a method of styling hair is provided which comprises applying a hair styling composition formulated in accordance with the invention to the hair desired to be styled and manipulating said hair to style it during or after said application. Heat may be applied to said hair during or following said application.

In accordance with the invention, there is provided a method of making a hair styling composition of the type containing a plurality of polymers and at least one solvent comprising adding a solvent to a vessel, adding one polymer and stirring until a clear mixture is obtained, adding another polymer and stirring until a clear mixture is obtained, and adding succeeding polymers, if any, one at a time and stirring until all desired polymers have been added and a clear mixture is obtained.

DESCRIPTION OF THE PREFERRED EMBODIMENTS OF THE PRESENT INVENTION

Embodiments of the invention provide a nonaqueous hair styling composition and a method of making and using the hair styling composition. The nonaqueous hair styling composition includes at least one vinyl copolymer and at least one nonaqueous solvent. The preferred vinyl copolymer is vinyl caprolactam/PVP/dimethylaminoethyl methacrylate copolymer. The preferred nonaqueous solvent is Dipropylene glycol. In addition, the nonaqueous hair styling composition optionally includes a urethane copolymer, a polyester, and a second nonaqueous solvent. If desired, additional nonaqueous additives may also be added to the hair styling composition. The nonaqueous additives may include, but are not limited to, other film formers (i.e., hair fixatives), viscosity controlling agents, humectants, occlusives, hair conditioning agents, sunscreens, emollients, antistatic agents, fragrances, natural oils, aliphatic hydrocarbons, silicones, and other additives that add or enhance the desired properties of the nonaqueous hair styling composition.

Embodiments of the invention also provide a new method of applying a hair styling composition to hair. The method includes applying the hair styling composition of the invention to at least a portion of hair. The method optionally includes the step of applying heat to the hair.

Embodiments of the invention also provide a new method of making a hair styling composition. The method includes mixing copolymer with solvent.

The nonaqueous hair styling composition obtained in accordance with embodiments of the invention can be applied to a portion of hair to assist in obtaining a desired style or configuration. The nonaqueous hair styling composition imparts hold, shine, manageability, body, weight, frizz control, conditioning and moisturization to the hair without making the hair unmanageably stiff, brittle, sticky, greasy, tacky, soft or appear excessively coated. The nonaqueous hair styling composition can be combed or brushed without or with limited loss of hold or without the possibility of flaking.

The hair styling composition obtained in accordance with embodiments of the invention may be used on all hair types including, but not limited to, straight, curly, wavy, fine, coarse, normal, frizz-prone hair, color treated or highlighted. The hair styling composition allows hair to be shaped into a generally flat or generally straight style or configuration without the need to apply a flat iron to the hair. The hair styling composition may be used as a finishing product on wet or dry hair. Once the hair styling composition has been applied to the hair, heat is used to accelerate film formation by the hair styling composition. The heat can be from any heating source which is suitable for application to hair such as a hair dryer. Once dried, the hair styling composition encases each hair fiber with a coating and creates a glossy sheen or finish. The nonaqueous hair styling composition provides hold, shine, manageability, body, weight, frizz control, condition and moisturization to the hair without making the hair unmanageably stiff, brittle, sticky, greasy, tacky, or excessively coated. Further combing, brushing or styling is possible once the hair styling composition has been applied to the hair. The hair styling composition assists in imparting a temporary style or configuration to the hair and can be removed from the hair with water and detergents.

The term "nonaqueous hair styling composition" used herein refers to any hair care product, including but not limited to, styling gels, styling lotions, styling serums, styling creams, styling laminators, styling fixatives such as hair spray and any combinations thereof which do not contain water. The term "hair" refers to both human hair and animal hair.

The nonaqueous hair styling composition can be applied in various manners to the hair. The hair styling composition may be manually applied to the hair surface in liquid, serum, cream, or gel form. The hair styling composition can also be applied to the hair using a pump, aerosol, or any targeted applicator.

The nonaqueous hair styling composition in accordance with embodiments of the invention can be formulated over a wide compositional range. For example, Table I below exemplifies the compositional ranges in which the hair styling composition can be prepared. It should be recognized, however, that a hair styling composition may also be formulated outside the exemplified compositional ranges. It should also be recognized that while the compounds in Table I are listed with respect to one function, the compounds may serve additional functions. Sometimes one compound may be capable of multiple functions. Any of the listed compounds may be used in embodiments of the invention without regard to their function.

TABLE I

| Component (percent by weight) | Range (percent by weight) | Preferred Range (percent by weight) | More Preferred Range (percent by weight) |
| --- | --- | --- | --- |
| Vinyl Copolymer | 2.5–15 | 3.0–10 | 5–10 |
| First Nonaqueous Solvent | 40–97.5 | 45–97 | 50–95 |
| Optional Ingredients | | | |
| Urethane Copolymer | 0.1–6.0 | 0.2–4.0 | 0.2–2.0 |
| Polyester | 0.1–6.0 | 0.2–4.0 | 0.2–3.0 |
| Second Nonaqueous Solvent | 0–40 | 2.5–35 | 10.0–30 |
| Film Former | 1.0–10 | 1.5–7.5 | 2.0–5.0 |
| Viscosity Controlling Agent | 0.1–1.0 | 0.15–0.75 | 0.15–0.50 |
| Humectant | 0.2–5.0 | 0.5–3.5 | 0.5–2.0 |
| Occlusive | 0.2–5.0 | 0.5–3.5 | 0.5–2.0 |
| Hair Conditioning Agent | 0.1–2.0 | 0.1–1.5 | 0.2–1.0 |
| Sunscreen | 0.1–2.0 | 0.2–1.5 | 0.2–1.0 |
| Emollient | 0.1–5.0 | 0.1–3.0 | 0.2–3.0 |
| Antistatic Agent | 0.1–1.0 | 0.2–0.8 | 0.2–0.5 |
| Fragrance | 0.05–0.2 | 0.05–0.15 | 0.05–0.10 |

The nonaqueous hair styling composition includes a vinyl copolymer. Suitable vinyl copolymers for use in the nonaqueous hair styling composition are capable of providing hold to the hair styling composition. Examples of suitable vinyl copolymers include, but are not limited, to PVP/VA/vinyl propionate copolymer, PVP/VA copolymer; Sodium acrylate/vinyl alcohol copolymer; Stearylvinyl ether/MA copolymer; VA/crotonates/vinyl neodecanoate copolymer; VA/crotonates/vinyl propionate copolymer; VA/isobutyl maleate/vinyl neodecanoate copolymer; VA/vinyl butyl benzoate/crotonates copolymer; Vinyl caprolactam/PVP/dimethylaminoethyl methacrylate copolymer; and mixtures thereof. In some embodiments, the vinyl polymer used in the hair styling composition is Vinyl caprolactam/PVP/dimethylaminoethyl methacrylate copolymer as identified by its INCI name. One example of a suitable Vinyl caprolactam/PVP/dimethylaminoethylmethacrylate copolymer is a Vinyl caprolactam/PVP/dimethylaminoethylmethacrylate copolymer in ethanol such as Gaffix® VC-713. Gaffix® VC-713 is a vinyl caprolactam based terpolymer which contains vinylpyrrolidone and dimethylaminoethylmethacrylate in ethanol SDA-40B made by International Specialty Products, Co., Ltd. It is understood that the vinyl caprolactam/PVP/dimethylaminoethylmethacrylate polymer may be in an alternate form as a powder terpolymer.

The nonaqueous hair styling composition may also include a nonaqueous solvent which is a low volatility, polyhydric C2–C6 alcohol having a boiling point of at least 200° C. The polyhydric alcohol must be soluble in water, ethanol, and oil and preferably have a refractive index above 1.41. The selection of the polyhydric C2–C6 alcohol for use in the hair styling composition depends a variety of factors such as the flowability of the hair styling composition, desired viscosity of the hair styling composition, toxicity and safety of the hair styling composition and solubility or dispersibility of polymers to be utilized. Suitable polyhydric C2–C6 alcohols for use in the hair styling composition are capable of adding gloss to the hair and assisting in providing weight, flexibility and moisture retention to the hair. Examples of suitable polyhydric C2–C6 alcohols for use in the hair styling composition include, but are not limited to propylene glycol, glycerin, dipropylene glycol, butylene glycol, pentylene glycols, hexylene glycols, and C2–C6 polyhydric alcohols containing a ether linkage and mixtures thereof. In some embodiments, the polyhydric C2–C6 alcohol used in the nonaqueous hair styling composition is dipropylene glycol such as fragrance grade dipropylene glycol (low odor) made by Arco Chemical Company.

The hair styling composition may optionally include a second nonaqueous solvent. The second solvent is a monohydric C2–C3 alcohol which is soluble in water and oil. The selection of the monohydric alcohol for use in the hair styling composition depends a variety of factors such as volatility, toxicity and viscosity. Suitable monohydric alcohols for use in the hair styling composition are capable of controlling the viscosity and the dry-time of the hair styling composition. Examples of suitable monohydric alcohols for use in the hair styling composition include, but are not limited to, ethanol, 1-propanol, 2-propanol and monohydric C2–C3 alcohols containing an ether linkage and mixtures thereof. In some embodiments, the monohydric alcohol used in the nonaqueous hair styling composition is denatured alcohol such as SDA 40 B alcohol (anhydrous) made by Grain Processing Corporation.

In addition the nonaqueous hair styling composition in accordance with the embodiments of the invention optionally includes a urethane copolymer. Suitable urethane copolymers for use in the hair styling composition are water and or alcohol soluble and contain but are not limited to contain pendant hydroxyl groups as well as, esters, silicones, triglycerides, tertiary amines and Isophorone Diisocyanate functionalities. The selection of the urethane copolymer for use in the hair styling composition depends on a variety of factors such as the ability of the urethane copolymer to aid in adding weight, conditioning and smoothing of hair surface and easy wash off of the composition. Examples of suitable urethane copolymers for use in the hair styling composition include, but are not limited to, a series of polyhydric alcohols, esters, silicones, triglycerides and amines copolymerized with isophorone diisocyanate (IPDI) radical.

In some embodiments, the urethane copolymer used in the hair styling composition is glycereth-7-diglycerol-PEG-15 cocamine/IPDI copolymer as identified by its proposed INCI name. One example of a suitable glycereth-7-diglycerol-PEG-15 cocamine/IPDI copolymer is Polyderm PPI-G7-CA. Polyderm PPI-G7-CA is a polyurethane derived from copolymerized glycereth, diglycerol and cocamine and is made by Alzo International Inc.

Other examples of suitable urethane copolymers for use in the hair styling composition include, but are not limited to Polyderm PPI-CO, Polyderm PPI-GH, Polyderm PPI-CA-15, Polyderm PPI-SA, Polyderm PPI-SA-15, Polyderm PPI-SA-15-D, Polyderm PPI-PE, Polyderm PPI-SI-WS, Polyderm PPI-TA, Polyderm PPI-200 and mixtures thereof.

In addition, the nonaqueous hair styling composition in accordance with the embodiments of the invention optionally includes a polyester. Suitable polyesters for use in the hair styling composition are oil soluble or dispersible polymers (hydrophobic) that generically can be described as saturated crosslinked hydroxy functional polyesters. The selection of a polyester for use in the hair styling composition depends on a variety of factors such as the ability of the polyester to aid in providing gloss and adherence to the hair surface and its ability to impart water resistance properties to the composite polymeric film left on the surface of hair. Suitable polyesters for use in the hair styling composition include, but are not limited to, adipic acid/diethylene glycol/glycerin crosspolymer, tripentanediol/adipic acid/glycerin crosspolymer, tripentanediol/adipic acid/isononanoic acid crosspolymer, tripentanediol/adipic acid copolymer, and mixtures thereof.

In some embodiments, the polyester used in the hair styling composition is trimethylpentanediol/adipic acid/glycerin crosspolymer as identified by its proposed INCI name. One example of a suitable trimethylpentanediol/adipic acid/glycerin crosspolymer is Lexorez 200. Lexorez 200 is a crosspolymer and is made by Inolex Corporation. Other examples of suitable polyesters for use in the hair styling composition include, but are not limited to, Lexorez 100, Lexorez TC-8, Lexorez TL-8 and mixture thereof.

To formulate the nonaqueous hair styling composition, additional nonaqueous ingredients may be added. These additional nonaqueous ingredients may include, but are not limited to, film formers (i.e., hair fixatives), viscosity controlling agents, humectants, occlusives, hair conditioning agents, sunscreens, emollients, antistatic agents, fragrances, natural oils, aliphatic hydrocarbons, silicones and other additives which add or enhance the desired properties of the nonaqueous hair styling composition.

In some embodiments of the nonaqueous hair styling composition, additional film formers or hair fixatives may be used to aid in providing hold to the hair. Any alcohol soluble film former or hair fixative may be used in embodiments of the invention. Suitable film formers or hair fixatives include, but are not limited to, the following compounds identified by their respective INCI names: Acrylamide/sodium acrylate copolymer; Acrylamides/acrylates/DMAPA/methoxy PEG methacrylate copolymer; Acrylamides copolymer; Acrylates/acetoacetoxyethyl methacrylate copolymer; Acrylates/acrylamide copolymer; Acrylates/ammonium methacrylate copolymer, Acrylates/$C_{10-30}$ alkyl acrylate crosspolymer; Acrylates/diacetoneacrylamide copolymer; Acrylates/octylacrylamide copolymer; Acrylates/PVP copolymer; Acrylates/steareth-50 acrylate copolymer; Acrylates/VA copolymer; Acrylates/VA crosspolymer; Acrylates copolymer; Acrylic acid/acrylonitrogens copolymer; Adipic acid/diethylene glycol/glycerin crosspolymer; Adipic acid/diethylenetriamine copolymer; Adipic acid/dimethylaminohydroxypropyl diethylenetriamine copolymer; Adipic acid/epoxypropyl diethylenetriamine copolymer; Allyl stearate/VA copolymer; Aminoethylacrylate phosphate/acrylates copolymer; Behenyl/isostearyl beeswax; Benzoic acid/phthalic anhydride/pentaerythritol/neopentyl glycol/palmitic acid copolymer; Butadiene/acrylonitrile copolymer; Butyl ester of ethylene/MA copolymer; Butyl ester of PVM/MA copolymer; Butylated PVP; Carnauba; Cetyl hydroxyethylcellulose; Chitosan succinamide; Corn starch/acrylamide/sodium acrylate copolymer;

Diethylene glycolamine/epichlorohydrin/piperazine copolymer; Dilinoleic acid/ethylenediamine copolymer; Dimethicone/mercaptopropyl methicone copolymer; Dimethicone/sodium PG-propyldimethicone thiosulfate copolymer; DMAPA acrylates/acrylic acid/acrylonitrogens copolymer; Dodecanedioic acid/cetearyl alcohol/glycol copolymer; Ethyl ester of PVM/MA copolymer; Ethylcellulose; Ethylene/acrylic acid/VA copolymer; Ethylene/acrylic acid copolymer; Ethylene/MA copolymer; Ethylene/propylene copolymer; Ethylene/VA copolymer; Glyceryl polyacrylate; Glycosaminoglycans; Hydrogenated styrene/butadiene copolymer; Hydrogenated styrene/methyl styrene/indene copolymer; Hydroxyethylcellulose; Hydroxypropylcellulose; Isopropyl ester of PVM/MA copolymer; Lauryl acrylate/VA copolymer; Methyl methacrylate crosspolymer; Octylacrylamide/acrylates/butylaminoethyl methacrylate copolymer; Polyacrylic acid; Polydimethylaminoethyl methacrylate; Polyethylacrylate; Polyethylene; Polyethylene terephthalate; Polyglucuronic acid; Polyglycerylmethacrylate; Polyisobutene; Polymethyl acrylate; Polymethyl methacrylate; Polyoxyisobutylene/methylene urea copolymer; Polypropylene; Polyquaternium-11; Polystyrene; Polyvinyl acetate; PPG-26/TDI copolymer; PPG-51/SMDI copolymer; PVM/MA copolymer; PVP; PVP/decene copolymer; PVP/dimethylaminoethylmethacrylate copolymer; PVP/eicosene copolymer; PVP/hexadecene copolymer; PVP/VA/itaconic acid copolymer; PVP/VA copolymer; Starch/acrylates/acrylamide copolymer; Starch diethylaminoethyl ether; Steareth-10 allyl ether/acrylates copolymer; Styrene/acrylates/acrylonitrile copolymer; Styrene/acrylates/ammonium methacrylate copolymer; Styrene/allyl benzoate copolymer; Styrene/MA copolymer; Styrene/PVP copolymer; VA/butyl maleate/isobornyl acrylate copolymer; VA/crotonates/methacryloxybenzophenone-1 copolymer; VA/crotonates copolymer; VA/DBM copolymer; Vinyl acetate; and mixtures thereof.

In some embodiments of the nonaqueous hair styling composition, one or more viscosity controlling agents are added to the hair styling composition to increase or decrease the desired viscosity of the hair styling composition. Any viscosity controlling agent may be used in embodiments of the invention. Suitable viscosity increasing agents include, but are not limited to, the following compounds identified by their respective INCI names:

7-dehydrocholesterol; Acrylates/diacetoneacrylamide copolymer; Acrylates/steareth-20 methacrylate copolymer; Acrylates/steareth-50 acrylate copolymer; Acrylates/VA copolymer; Behenyl beeswax; Butadiene/acrylonitrile copolymer; Butoxy chitosan; Butyl methacrylate; C12–13 alcohols; C12–15 alcohols; C12–16 alcohols; C18–38 alkyl; C24–54 acid ester; C9–11 alcohols; Caprylic alcohol; Carbomer; Carboxymethyl hydroxyethylcellulose; Carboxymethyl hydroxypropyl guar; Carrageenan; Cellulose; Cellulose gum; Cera microcristallina; Ceresin; Cerotic acid; Cetearyl alcohol; Cetyl alcohol; Cetyl laurate; Cholesteryl hydroxystearate; Decyl alcohol; Dibenzylidene sorbitol; Diglyceryl stearate malate; Dipropylene glycol salicylate; Dodecanedioic acid/cetearyl alcohol/glycol copolymer; Erucamide; Ethyl methacrylate; Ethylcellulose; Ethylene dioleamide; Ethylene distearamide; Glyceryl polymethacrylate; Glyceryl triacetyl hydroxystearate; Glyceryl triacetyl ricinoleate; Glycol dibehenate; Glycol dilaurate; Glycol dioctanoate; Glycol dioleate; Glycol distearate; Glycol ditallowate; Hectorite; Hexanediol distearate; Hydrogenated butylene/ethylene/styrene copolymer; Hydrogenated castor oil; Hydrogenated castor oil hydroxystearate; Hydrogenated castor oil isostearate; Hydrogenated castor oil stearate; Hydrogenated ethylene/propylene/styrene copolymer; Hydrogenated microcrystalline wax; Hydrogenated palm kernel glycerides; Hydrogenated palm kernel oil; Hydrogenated rice bran wax; Hydrogenated tallow amide; Hydrogenated vegetable glyceride; Hydroxybutyl methylcellulose; Hydroxyethylcellulose; Hydroxypropyl methylcellulose; Isobutylene/isoprene copolymer; Isobutylene/MA copolymer; Isocetyl alcohol; Isocetyl stearoyl stearate: Isostearyl alcohol; Laneth-10; Laneth-15; Laneth-20; Laneth-5; Lauramide; Lauryl alcohol; Lauryl methacrylate; Methylcellulose; Microcrystalline cellulose; Myristyl alcohol; Nylon-11; Nylon-12; Octadecene/MA copolymer; Octyldodecyl stearoyl stearate; Oleyl alcohol; Ozokerite; Paraffin; Peg-150 distearate; Peg-175 distearate; Polyacrylic acid; Polybutene; Polyethylene; Polyisobutene; Polymethacrylic acid; Polymethyl methacrylate; Polyoxymethylene urea; Polypropylene; Polyvinyl alcohol; Polyvinyl butyral; Polyvinyl laurate; Propylene glycol alginate; Propylene glycol dicaprylate; Propylene glycol diisononanoate; Propylene glycol dilaurate; Propylene glycol dipelargonate; Propylene glycol distearate; PVP/eicosene copolymer; PVP/hexadecene copolymer; PVP/VA/vinyl propionate copolymer; Silica; Stearyl alcohol; Stearyl erucamide; Stearyl stearate; Stearyl stearoyl stearate; Stearylvinyl ether/MA copolymer; Styrene/acrylates/acrylonitrile copolymer; Styrene/allyl benzoate copolymer; Synthetic beeswax; Synthetic; Synthetic wax; Tetradecyleicosanol; Tetradecyloctadecanol; Tridecyl alcohol; Trihydroxystearin; Triisostearin; Triisostearyl trilinoleate; Trilaurin; Trilinoleic acid; Trilinolein; Trimyristin; Triolein; Tripalmitin; Tristearin; Vinyldimethicone; Xanthan gum; *Zea mays;* and mixtures thereof.

In some embodiments of the nonaqueous hair styling composition, additional humectants are added to the hair styling composition to aid the hair styling composition in holding or retaining moisture. Any humectant may be used in embodiments of the invention. Suitable humectants include, but are not limited to, the following compounds identified by their INCI names: 1,2,6-hexanetriol; Acetamide MEA; Arachidyl glycol; Arginine PCA; Butoxypropanol; Butylene glycol; Butyloctanol; Capryl glycol; Carboxymethyl chitosan succinamide; Chitosan PCA; Cyclomethicone; Diglycerin; Dimethicone copolyol acetate; Dimethicone copolyol adipate; Dimethicone copolyol behenate; Dimethicone copolyol butyl ether; Dimethicone copolyol hydroxystearate; Dimethicone copolyol isostearate; Dimethicone copolyol laurate; Dimethicone copolyol methyl ether; Dimethicone copolyol phosphate; Dimethicone copolyol stearate; Dimethicone copolyolamine; Dimethicone silylate; Dimethyl imidazolidinone; Dimethylsilanol hyaluronate; Erythritol; Ethoxydiglycol; Fructose; Glucamine; Gluconic acid; Glucose; Glucose glutamate; Glucuronic acid; Glutamic acid; Glutamic acid; Glycereth-12; Glycereth-20; Glycereth-26; Glycereth-7; Glycerin; Glycogen; Glycyrrhetinyl stearate; Glycyrrhizic acid; Heilmoor clay; Hexacosyl glycol; Hexanediol beeswax; Hexanetriol beeswax; Hexyldecanol; Hyaluronic acid; Hydrogenated honey; Hydrogenated starch hydrolysate; Hydrolyzed elastin; Hydrolyzed glycosaminoglycans; Hydrolyzed keratin; Hydrolyzed silk; Hydrolyzed soy protein; Hydrolyzed wheat protein/dimethicone copolyol phosphate copolymer; Hydroxyethyl sorbitol; Inositol; Inositol hexa-PCA; Isopropyl hydroxybutyramide dimethicone copolyol; Lactic acid; Lactitol; Lactose; Lauryl PCA; Lysine PCA; Lysine PCA; Lysine PCA; Maltitol; Mannitol; Mel; Menthyl PCA; Methyl gluceth-10; Methyl gluceth-20; Methyl glucose dioleate; Polydextrose; Polyglucuronic acid; Polyglycerin-3; Polyglyceryl sorbitol; Polysilicone-1; Polysilicone-2;

PPG-20 methyl glucose ether distearate; Propylene glycol; Silk amino acids; Sodium carboxymethyl chitin; Sodium PCA methylsilanol; Sodium PG-propyl thiosulfate dimethicone; Sodium polyglutamate; Sorbitol; Soy sterol; Sucrose; Sulfated castor oil; Tea-PCA; Trehalose; Tricontanyl PVP; Urea; *Zea mays*; and mixtures thereof.

In some embodiments, one or more occlusives are added to the nonaqueous hair styling composition to create a moisture barrier and smooth hair surface. Any occlusive may be used in embodiments of the invention. Suitable occlusives include, but are not limited to, the following compounds identified by their respective INCI names: mineral oil, dimethicone, dimethiconol, petrolatum and mixtures thereof.

In some embodiments, one or more hair conditioning agents are added to the nonaqueous hair styling composition to smooth surface and to lessen static charge. Substantially, any formulation soluble hair conditioning agent may be used in embodiments of the invention.

In some embodiments, one or more sunscreens are added to the nonaqueous hair styling composition to aid in filtering ultraviolet rays. Substantially, any sunscreen may be used in embodiments of the invention. For example, suitable sunscreens include, but are not limited to: any alcohol or oil soluble approved sunscreen suitable for use in skin or hair care products listed in the FDA Sunscreen Monograph.

In some embodiments, one or more emollients are added to the nonaqueous hair styling composition to aid in softening the hair or for removing a greasy feel from the hair styling composition. Substantially, any emollient may be used in embodiments of the invention. For example, suitable emollients include, but are not limited to the following compounds identified by their INCI names: Acetylated hydrogenated cottonseed glyceride; Acetylated hydrogenated tallow glyceride; Acetylated hydrogenated tallow glycerides; Acetylated lanolin; Acetylated lanolin alcohol; Acetylated palm kernel glycerides; Amino bispropyl dimethicone; Apricot kernel oil PEG-6 esters; Behenamidopropyl dimethylamine; Behenyl/isostearyl beeswax; $C_{10-30}$ cholesterol/lanosterol esters; alkylbenzoate; Canola oil glyceride; Caprylic/capric/diglyceryl succinate; Caprylic/capric glycerides; Caprylic/capric triglyceride PEG-4 esters; Cetearyl octanoate; Cetearyl stearate; Cetyl dimethicone copolyol; Cholesterol; Cholesteryl stearate; Cocoglycerides; Coconut alcohol; Corn glycerides; Corn oil PEG-6 esters; Dicocodimethylamine dilinoleate; Diethylaminoethyl PEG-5 laurate; Diethylaminoethyl stearate; Dihydrogenated tallow methylamine; Dihydrolanosterol; Dimethoxysilyl ethylenediaminopropyl dimethicone; Dioctyldodecyl stearoyl glutamate; Dipentaerythrityl hexacaprylate/hexacaprate; Dipentaerythrityl hexahydroxystearate; Dipentaerythrityl hexahydroxystearate/isostearate; Dipentaerythrityl hexahydroxystearate/stearate/rosinate; Dipentaerythrityl pentaoctanoate/behenate; Diphenyl dimethicone; Ethylene dihydrogenated tallowamide; Fluoro $C_{2-8}$ alkyldimethicone; Glycereth-20 stearate; Glycereth-25 PCA isostearate; Glycereth-26 phosphate; Glycereth-5 lactate; Glycereth-7 benzoate; Glycereth-7 diisononanoate; Glycereth-8 hydroxystearate; Glyceryl/sorbitol oleate/hydroxystearate; Glyceryl arachidate; Glyceryl arachidonate; Glyceryl behenate; Glyceryl caprylate; Glyceryl caprylate/caprate; Glyceryl citrate/lactate/linoleate/oleate; Glyceryl cocoate; Glyceryl diisostearate; Glyceryl dilaurate; Glyceryl dipalmitate; Glyceryl erucate; Glyceryl glycyrrhetinate; Glyceryl hydroxystearate; Glyceryl isopalmitate; Glyceryl isostearate; Glyceryl isotridecanoate/stearate/adipate; Glyceryl lanolate; Glyceryl laurate; Glyceryl linoleate; Glyceryl myristate; Glyceryl oleate; Glyceryl palmitoleate; Glyceryl sesquioleate; Glyceryl stearate; Glyceryl stearate diacetate; Glyceryl stearate lactate; Glycol octanoate; Glycol oleate; Glycol palmitate; Glycol ricinoleate; Glycol stearate; Hexyldeceth-20; Hydrogenated castor oil; Hydrogenated palm oil; Hydrogenated peanut oil; Hydrogenated soybean glycerides; Hydrogenated vegetable glycerides; Hydroxycetyl isostearate; Hydroxylated lanolin; Isopropyl lanolate; Isopropyl palmitate; Isosteareth-10 stearate; Isostearic/myristic glycerides; Isostearic acid; Isostearoyl isostearyl stearate; Lanolin alcohol; Laurylmethicone copolyol; Lecithin; Linseed acid; Lysolecithin; Methyl gluceth-10; Methyl glucose isostearate; Methyl glucose laurate; Methyl glucose sesquicaprylate/sesquicaprate; Methyl glucose sesquicocoate; Methyl glucose sesquiisostearate; Methyl glucose sesquilaurate; Methyl glucose sesquioleate; Methyl glucose sesquistearate; Methyl isostearate; Methylsilanol PEG-7 glyceryl cocoate; Neopentyl glycol diisostearate; Neopentyl glycol dilaurate; Octoxyglyceryl behenate; Octoxyglyceryl palmitate; Octyl linoleoyl stearate; Octyldecyl oleate; Oleyl alcohol; Olive oil PEG-10 esters; Palm glyceride; Palm glycerides; Palm kernel alcohol; Palm kernel glycerides; Peanut glycerides; PEG-10 castor oil; PEG-10 cocoate; PEG-10 dioleate; PEG-10 glyceryl oleate; PEG-10 glyceryl stearate; PEG-10 hydrogenated lanolin; PEG-10 hydrogenated tallow amine; PEG-10 isolauryl thioether; PEG-10 isostearate; PEG-10 lanolate; PEG-10 lanolin; PEG-10 laurate; PEG-10 oleate; PEG-10 olive glycerides; PEG-10 sorbitan laurate; PEG-10 soya sterol; PEG-10 soyamine; PEG-10 stearamine; PEG-10 stearate; PEG-10 tallate; PEG-10 tallow aminopropylamine; PEG-100 castor oil; PEG-100 hydrogenated castor oil; PEG-100 lanolin; PEG-11 avocado glycerides; PEG-11 babassu glycerides; PEG-11 castor oil; PEG-11 cocamide; PEG-11 oleate; PEG-11 tallow amine; PEG-12 beeswax; PEG-12 dilaurate; PEG-12 dioleate; PEG-12 distearate; PEG-12 ditallate; PEG-12 glyceryl dioleate; PEG-12 glyceryl laurate; PEG-12 isostearate; PEG-12 laurate; PEG-12 oleate; PEG-12 palm kernel glycerides; PEG-12 stearate; PEG-12 tallate; PEG-120 distearate; PEG-120 jojoba acid; PEG-120 jojoba alcohol; PEG-120 methyl glucose dioleate; PEG-120 propylene glycol stearate; PEG-13 diphenylol propane; PEG-13 hydrogenated tallow amide; PEG-13 mink glycerides; PEG-13 octanoate; PEG-14 avocado glycerides; PEG-14 laurate; PEG-14 oleate; PEG-14 stearate; PEG-14 tallate; PEG-140 glyceryl tristearate; PEG-15 butanediol; PEG-15 castor oil; PEG-15 cocamine; PEG-15 cocamine oleate/phosphate; PEG-15 cocoate; PEG-15 cocomonium chloride; PEG-15 cocopolyamine; PEG-15 glyceryl isostearate; PEG-15 glyceryl laurate; PEG-15 glyceryl oleate; PEG-15 glyceryl ricinoleate; PEG-15 hydrogenated tallow amine; PEG-15 hydroxystearate; PEG-15 jojoba acid; PEG-15 jojoba alcohol; PEG-15 lanolate; PEG-15 oleamine; PEG-15 oleate; PEG-15 soyamine; PEG-15 stearamine; PEG-15 tallow aminopropylamine; PEG-15 tallow polyamine; PEG-150 dilaurate; PEG-150 dioleate; PEG-150 distearate; PEG-150 lanolin; PEG-150 pentaerythrityl tetrastearate; PEG-16 hydrogenated castor oil; PEG-16 oleate; PEG-16 soya sterol; PEG-16 tallate; PEG-175 distearate; PEG-18 castor oil dioleate; PEG-18 glyceryl oleate/cocoate; PEG-18 palmitate; PEG-18 stearate; PEG-2 castor oil; PEG-2 cocamine; PEG-2 cocomonium chloride; PEG-2 diisononanoate; PEG-2 dilaurate; PEG-2 dioctanoate; PEG-2 distearate; PEG-2 hydrogenated castor oil; PEG-2 hydrogenated tallow amine; PEG-2 laurate; PEG-2 laurate SE; PEG-2 oleamide; PEG-2 oleamine; PEG-2 oleammonium chloride; PEG-2 oleate; PEG-2 oleate SE; PEG-2 ricinoleate; PEG-2 sorbitan isostearate; PEG-2 soyamine; PEG-2 stearamine; PEG-2 stearate; PEG-2 stearate SE; PEG-2 stearmonium chloride; PEG-20 almond glycerides; PEG-20 beeswax; PEG-20 castor oil; PEG-20 cocamide; PEG-20 cocamine; PEG-20 corn glycerides; PEG-20 dilaurate; PEG-20 dioleate; PEG-20 distearate; PEG-20 evening primrose glycerides; PEG-20 glyceryl laurate; PEG-20 glyceryl oleate; PEG-20 glyceryl ricinoleate; PEG-20 glyceryl stearate; PEG-20 hydrogenated castor oil; PEG-20 hydrogenated lanolin; PEG-20 hydrogenated palm oil glycerides; PEG-20 hydrogenated tallow amine; PEG-20 lanolate; PEG-20 lanolin; PEG-20 laurate; PEG-20 mannitan laurate; PEG-20 methyl glucose distearate; PEG-20 methyl glucose sesquicaprylate/sesquicaprate; PEG-20 methyl glucose sesquilaurate; PEG-20 methyl glucose sesquistearate; PEG-20 myristate; PEG-20 oleate; PEG-20 palmitate; PEG-20 sorbitan beeswax; PEG-20 sorbitan cocoate; PEG-20 sorbitan isostearate; PEG-20 stearate; PEG-20 tallate; PEG-20 tallowate; PEG-20-PPG-10 glyceryl stearate; PEG-200 castor oil; PEG-200 glyceryl tallowate; PEG-200 hydrogenated castor oil; PEG-200 montanate; PEG-200 trihydroxystearin; PEG-22/dodecyl glycol copolymer; PEG-23 glyceryl laurate; PEG-23 oleate; PEG-23 stearate; PEG-24 hydrogenated lanolin; PEG-24 lanolin; PEG-25 castor oil; PEG-25 glyceryl oleate; PEG-25 glyceryl stearate; PEG-25 glyceryl trioleate; PEG-25 hydrogenated castor oil; PEG-25 phytosterol; PEG-25 propylene glycol stearate; PEG-25 soya sterol; PEG-25 stearate; PEG-26 castor oil; PEG-26 jojoba acid; PEG-26 jojoba alcohol; PEG-27 lanolin; PEG-28 glyceryl tallowate; PEG-29 castor oil; PEG-3/PPG-2 glyceryl/sorbitol hydroxystearate/isostearate; PEG-3 castor oil; PEG-3 cocamide; PEG-3 cocamine; PEG-3 dipalmitate; PEG-3 distearate; PEG-3 lanolate; PEG-3 lauramide; PEG-3 oleamide; PEG-3 oleate; PEG-3 sorbitan oleate; PEG-3 sorbitan stearate; PEG-3 tallow aminopropylamine; PEG-30 castor oil; PEG-30 dipolyhydroxystearate; PEG-30 glyceryl cocoate; PEG-30 glyceryl laurate; PEG-30 glyceryl oleate; PEG-30 glyceryl stearate; PEG-30 hydrogenated castor oil; PEG-30 hydrogenated lanolin; PEG-30 hydrogenated tallow amine; PEG-30 lanolin; PEG-30 oleamine; PEG-30 sorbitan tetraoleate; PEG-30 sorbitol tetraoleate laurate; PEG-30 soya sterol; PEG-30 stearate; PEG-32 dilaurate; PEG-32 dioleate; PEG-32 distearate; PEG-32 oleate; PEG-32 stearate; PEG-33 castor oil; PEG-35 almond glycerides; PEG-35 castor oil; PEG-35 hydrogenated castor oil; PEG-35 lanolin; PEG-35 stearate; PEG-36 castor oil; PEG-36 oleate; PEG-36 stearate; PEG-4 castor oil; PEG-4 diheptanoate; PEG-4 dilaurate; PEG-4 dioleate; PEG-4 distearate; PEG-4 isostearate; PEG-4 lanolate; PEG-4 laurate; PEG-4 octanoate; PEG-4 oleamide; PEG-4 oleate; PEG-4 polyglyceryl-2 stearate; PEG-4 stearate; PEG-4 tallate; PEG-40 castor oil; PEG-40 glyceryl cocoate; PEG-40 hydrogenated castor oil; PEG-40 hydrogenated castor oil PCA isostearate; PEG-40 hydrogenated tallow amine; PEG-40 jojoba acid; PEG-40 jojoba alcohol; PEG-40 lanolin; PEG-40 olive glycerides; PEG-40 ricinoleamide; PEG-40 sorbitan diisostearate; PEG-40 sorbitan lanolate; PEG-40 sorbitan laurate; PEG-40 sorbitan perisostearate; PEG-40 sorbitan peroleate; PEG-40 sorbitan stearate; PEG-40 sorbitan tetraoleate; PEG-40 soya sterol; PEG-40 stearate; PEG-42 babassu glycerides; PEG-44 castor oil; PEG-45 hydrogenated castor oil; PEG-45 palm kernel glycerides; PEG-45 safflower glycerides; PEG-45 stearate; PEG-5 castor oil; PEG-5 cocamide; PEG-5 cocamine; PEG-5 cocoate; PEG-5 glyceryl sesquioleate; PEG-5 glyceryl stearate; PEG-5 glyceryl triisostearate; PEG-5 hydrogenated castor oil; PEG-5 hydrogenated corn glycerides; PEG-5 hydrogenated lanolin; PEG-5 hydrogenated tallow amine; PEG-5 lanolate; PEG-5 lanolin; PEG-5 lanolinamide; PEG-5 lauramide; PEG-5 octanoate; PEG-5 oleamide; PEG-5 oleamide dioleate; PEG-5 oleamine; PEG-5 oleate; PEG-5 sorbitan isostearate; PEG-5 soya sterol; PEG-5 soyamine; PEG-5 stearamine; PEG-5 stearate; PEG-5 tallate; PEG-5 tallow amide; PEG-5 tricaprylyl citrate; PEG-5 trimethylolpropane trimyristate; PEG-50 castor oil; PEG-50 hydrogenated castor oil; PEG-50 hydrogenated tallow amine; PEG-50 lanolin; PEG-50 shea butter; PEG-50 sorbitol hexaoleate; PEG-50 stearamine; PEG-50 stearate; PEG-50 tallow amide; PEG-54 castor oil; PEG-54 hydrogenated castor oil; PEG-55 castor oil; PEG-55 hydrogenated castor oil; PEG-55 lanolin; PEG-6 beeswax; PEG-6 caprylic/capric glycerides; PEG-6 cocamide; PEG-6 dilaurate; PEG-6 dioleate; PEG-6 distearate; PEG-6 isolauryl thioether; PEG-6 isopalmitate; PEG-6 isostearate; PEG-6 lauramide; PEG-6 laurate; PEG-6 laurate/tartarate; PEG-6 oleamide; PEG-6 oleate; PEG-6 palmitate; PEG-6 sorbitan beeswax; PEG-6 sorbitan oleate; PEG-6 sorbitan stearate; PEG-6 stearate; PEG-6 undecylenate; PEG-60 almond glycerides; PEG-60 castor oil; PEG-60 corn glycerides; PEG-60 evening primrose glycerides; PEG-60 hydrogenated castor oil; PEG-60 lanolin; PEG-60 sorbitan tetraoleate; PEG-60 sorbitan tetrastearate; PEG-66 trihydroxystearin; PEG-7 cocamide; PEG-7 glyceryl cocoate; PEG-7 hydrogenated castor oil; PEG-7 lanolate; PEG-7 oleamide; PEG-7 oleate; PEG-7 ricinoleate; PEG-7 stearate; PEG-7 tallow amine; PEG-70 hydrogenated lanolin; PEG-70 mango glycerides; PEG-75 castor oil; PEG-75 cocoa butter glycerides; PEG-75 dilaurate; PEG-75 dioleate; PEG-75 distearate; PEG-75 lanolin; PEG-75 lanolin oil; PEG-75 lanolin wax; PEG-75 propylene glycol stearate; PEG-75 shea butter glycerides; PEG-75 shorea butter glycerides; PEG-75 sorbitan lanolate; PEG-78 glyceryl cocoate; PEG-8 beeswax; PEG-8 behenate; PEG-8 $C_{12-18}$ ester; PEG-8 caprate; PEG-8 caprylate; PEG-8 caprylate/caprate; PEG-8 caprylic/capric glycerides; PEG-8 castor oil; PEG-8 cocoate; PEG-8 di/triricinoleate; PEG-8 dicocoate; PEG-8 diisostearate; PEG-8 dilaurate; PEG-8 dioleate; PEG-8 distearate; PEG-8 ditallate; PEG-8 glyceryl laurate; PEG-8 hydrogenated fish glycerides; PEG-8 hydrogenated tallow amine; PEG-8 isolauryl thioether; PEG-8 isostearate; PEG-8 laurate; PEG-8 myristate; PEG-8 oleate; PEG-8 propylene glycol cocoate; PEG-8 sesquilaurate; PEG-8 sesquioleate; PEG-8 sorbitan beeswax; PEG-8 soyamine; PEG-8 stearate; PEG-8 tallate; PEG-8 tallow amide; PEG-8 undecylenate; PEG-80 glyceryl cocoate; PEG-80 glyceryl tallowate; PEG-80 hydrogenated castor oil; PEG-80 methyl glucose laurate; PEG-80 sorbitan palmitate; PEG-85 lanolin; PEG-9 castor oil; PEG-9 cocoate; PEG-9 diethylmonium chloride; PEG-9 distearate; PEG-9 laurate; PEG-9 oleamide; PEG-9 oleate; PEG-9 stearamide carboxylic acid; PEG-9 stearate; Pentaerythrityl distearate; Pentaerythrityl tetraisostearate; Phosphatidylcholine; Polyglyceryl-10 decalinoleate; Polyglyceryl-10 decaoleate; Polyglyceryl-10 decastearate; Polyglyceryl-10 diisostearate; Polyglyceryl-10 dioleate; Polyglyceryl-10 distearate; Polyglyceryl-10 heptaoleate; Polyglyceryl-10 heptastearate; Polyglyceryl-10 isostearate; Polyglyceryl-10 laurate; Polyglyceryl-10 mono/dioleate; Polyglyceryl-10 myristate, Polyglyceryl-10 oleate; Polyglyceryl-10 pentaoleate; Polyglyceryl-10 pentastearate; Polyglyceryl-10 stearate; Polyglyceryl-10 tetraoleate; Polyglyceryl-10 trioleate; Polyglyceryl-10 tristearate; Polyglyceryl-2 caprate; Polyglyceryl-2 caprylate; Polyglyceryl-2 diisostearate; Polyglyceryl-2 dioleate; Polyglyceryl-2 distearate; Polyglyceryl-2 isopalmitate; Polyglyceryl-2 isostearate; Polyglyceryl-2 lanolin alcohol ether; Polyglyceryl-2 laurate;

Polyglyceryl-2 oleate; Polyglyceryl-2 oleyl ether; Polyglyceryl-2 sesquiisostearate; Polyglyceryl-2 sesquioleate; Polyglyceryl-2 sesquistearate; Polyglyceryl-2 sorbitan pentacaprylate; Polyglyceryl-2 sorbitan tetracaprylate; Polyglyceryl-2 stearate; Polyglyceryl-2 tetraisostearate; Polyglyceryl-2 tetrastearate; Polyglyceryl-2 triisostearate; Polyglyceryl-2-PEG-4 stearate; Polyglyceryl-3 beeswax; Polyglyceryl-3 caprate, Polyglyceryl-3 cetyl ether; Polyglyceryl-3 decyltetradecanol; Polyglyceryl-3 dicaprate; Polyglyceryl-3 diisostearate; Polyglyceryl-3 dioleate; Polyglyceryl-3 distearate; Polyglyceryl-3 hydroxylauryl ether; Polyglyceryl-3 isostearate; Polyglyceryl-3 laurate; Polyglyceryl-3 methylglucose distearate; Polyglyceryl-3 myristate; Polyglyceryl-3 oleate; Polyglyceryl-3 ricinoleate; Polyglyceryl-3 stearate; Polyglyceryl-3 stearate SE; Polyglyceryl-4 caprate; Polyglyceryl-4 cocoate; Polyglyceryl-4 isostearate; Polyglyceryl-4 laurate; Polyglyceryl-4 lauryl ether; Polyglyceryl-4 oleate; Polyglyceryl-4 oleyl ether; Polyglyceryl-4 stearate; Polyglyceryl-4-PEG-2 cocamide; Polyglyceryl-5 isostearate; Polyglyceryl-5 laurate; Polyglyceryl-5 oleate; Polyglyceryl-6 dioleate; Polyglyceryl-6 distearate; Polyglyceryl-6 hexaoleate; Polyglyceryl-6 isostearate; Polyglyceryl-6 laurate; Polyglyceryl-6 oleate; Polyglyceryl-6 pentaoleate; Polyglyceryl-6 pentastearate; Polyglyceryl-6 ricinoleate; Polyglyceryl-6 tristearate; Polyglyceryl-8 oleate; Polyglyceryl-8 stearate; PPG-1-PEG-9 lauryl glycol ether; PPG-10 cetyl ether; PPG-10 glyceryl ether; PPG-10 lanolin alcohol ether; PPG-10-buteth-9; PPG-10-ceteareth-20; PPG-12-buteth-12; PPG-12-buteth-16; PPG-12-laneth-50; PPG-12-PEG-50 lanolin; PPG-12-PEG-65 lanolin oil; PPG-15-buteth-20; PPG-15-PEG-11 hydrogenated lauryl alcohol ether; PPG-17-buteth-17; PPG-2 cocamine; PPG-2 isoceteth-20 acetate; PPG-2 lanolin alcohol ether; PPG-2 tallowamine; PPG-2-buteth-3; PPG-2-ceteareth-9; PPG-2-ceteth-10; PPG-2-ceteth-20; PPG-2-deceth-10; PPG-2-isodeceth-12; PPG-2-isodeceth-4; PPG-2-isodeceth-6; PPG-2-isodeceth-9; PPG-2-PEG-6 coconut oil esters; PPG-20 lanolin alcohol ether; PPG-20-buteth-30; PPG-20-decyltetradeceth-10; PPG-20-glycereth-30; PPG-20-PEG-20 hydrogenated lanolin; PPG-23-PEG-4 trimethylolpropane; PPG-24-buteth-27; PPG-24-glycereth-24; PPG-24-PEG-21 tallowaminopropylamine; PPG-25 diethylmonium chloride; PPG-25-laureth-25; PPG-26-buteth-26; PPG-27 glyceryl ether; PPG-28 cetyl ether; PPG-28-buteth-35; PPG-3 hydrogenated castor oil; PPG-3 myristyl ether; PPG-3-buteth-5; PPG-3-isosteareth-9; PPG-3-laureth-9; PPG-3-myreth-11; PPG-3-myreth-3; PPG-30 lanolin alcohol ether; PPG-33-buteth-45; PPG-4 myristyl ether; PPG-4-ceteareth-12; PPG-4-ceteth-1; PPG-4-ceteth-10; PPG-4-ceteth-5; PPG-40 diethylmonium chloride; PPG-40-PEG-60 lanolin oil; PPG-5 lanolate; PPG-5 lanolin alcohol ether; PPG-5 lanolin wax; PPG-5 lanolin wax glyceride; PPG-5 pentaerythrityl ether; PPG-5-buteth-7; PPG-5-ceteth-20; PPG-5-laureth-5; PPG-55 glyceryl ether; PPG-6 C12–18 pareth-11; PPG-6-decyltetradeceth-12; PPG-6-decyltetradeceth-20; PPG-6-decyltetradeceth-30; PPG-66-glycereth-12; PPG-7-buteth-10; PPG-8-ceteth-1; PPG-8-ceteth-10; PPG-8-ceteth-2; PPG-8-ceteth-20; PPG-8-ceteth-5; PPG-9-buteth-12; Propylene glycol dicocoate; Propylene glycol hydroxystearate; Propylene glycol isodeceth-12; Propylene glycol isodeceth-4; Propylene glycol isostearate; Propylene glycol laurate; Propylene glycol myristate; Propylene glycol oleate; Propylene glycol ricinoleate; Propylene glycol stearate; Ricinoleic acid; Ricinoleth-40; Safflower glyceride; Sorbeth-3 isostearate; Sorbitan caprylate; Sorbitan cocoate; Sorbitan diisostearate; Sorbitan dioleate; Sorbitan isostearate; Sorbitan laurate; Sorbitan oleate; Sorbitan palmitate; Sorbitan sesquiisostearate; Sorbitan sesquioleate; Sorbitan sesquistearate; Sorbitan stearate; Sorbitan triisostearate; Sorbitan trioleate; Sorbitan tristearate; Sorbityl acetate; Soy acid; Soy sterol; Soy sterol acetate; Soyaethyl morpholinium ethosulfate; Soyamidopropyl dimethylamine; Soyamine; Soyaminopropylamine; Stearamidopropyl dimethylamine stearate; Sucrose cocoate; Sucrose dilaurate; Sucrose distearate; Sucrose laurate; Sucrose myristate; Sucrose oleate; Sucrose palmitate; Sucrose polylaurate; Sucrose polylinoleate; Sucrose polyoleate; Sucrose polystearate; Sucrose ricinoleate; Sucrose stearate; Sucrose tetrastearate triacetate; Sucrose tribehenate; Sucrose tristearate; Sulfated castor oil; Sunflower seed oil glyceride; Sunflower seed oil glycerides; and mixtures thereof.

In some embodiments, one or more antistatic agents are added to the nonaqueous hair styling composition to aid in reducing static electricity. Any antistatic agent may be used in embodiments of the invention. For example, suitable antistatic agents include, but are not limited to, the following compounds identified by their INCI names: Acetamide MEA; Acetylated lanolin; Acetylated lanolin alcohol; Acetylated lanolin ricinoleate; Acetylmethionyl methylsilanol elastinate; Acrylamide/sodium acrylate copolymer; Acrylamides copolymer; Acrylates/ammonium methacrylate copolymer; Acrylates/PVP copolymer; Acrylates copolymer; Adipic acid/dimethylaminohydroxypropyl diethylenetriamine copolymer; Adipic acid/epoxypropyl diethylenetriamine copolymer; Alanine; Allantoin acetyl methionine; Aminoethylacrylate phosphate/acrylates copolymer; Amodimethicone; Amodimethicone/dimethicone copolyol; Arginine; Asparagine; Behenalkonium chloride; Behenamidopropyl dimethylamine; Behenamidopropyl dimethylamine behenate; Behenamidopropyl dimethylamine lactate; Behenamidopropyl ethyldimonium ethosulfate; Behenamidopropyl PG-dimonium chloride; Behenoyl PG-trimonium chloride; Behentrimonium methosulfate; Behenyl betaine; Benzyl nicotinate; Butyl ester of ethylene/MA copolymer; Butyl ester of PVM/MA copolymer; C12–15 alkyl salicylate; C12–16 alcohols; Canolamidopropyl ethyldimonium ethosulfate; Capryloyl collagen amino acids; Capryloyl hydrolyzed keratin; Capryloyl keratin amino acids; Ceresin; Cetethyl morpholinium ethosulfate; Cetrimonium tosylate; Cocamidopropyl ethyldimonium ethosulfate; Cocamidopropyl morpholine; Cocamidopropyl morpholine lactate; Corn starch/acrylamide/sodium acrylate copolymer; Cyclomethicone; Cysteine; Cystine; Cystine; Dicapryloyl cystine; Dicocodimonium chloride; Dicocoylethyl hydroxyethylmonium methosulfate; Didecyldimonium chloride; Diethyl aspartate; Diethyl glutamate; Diethylaminoethyl PEG-5 laurate; Dihydrogenated tallow benzylmonium chloride; Dihydrogenated tallow benzylmonium hectorite; Dihydrogenated tallow hydroxyethylmonium methosulfate; Dihydrogenated tallowamidoethyl hydroxyethylmonium chloride; Dihydrogenated tallowamidoethyl hydroxyethylmonium methosulfate; Dihydrogenated tallowdimonium chloride; Dihydrogenated tallowethyl hydroxyethylmonium methosulfate; Dihydrogenated tallowoylethyl hydroxyethylmonium methosulfate; Dihydroxyethyl C12–15 alkoxypropylamine oxide; Dihydroxyethyl cocamine oxide; Dihydroxyethyl soya glycinate; Dihydroxyethyl stearamine oxide; Dihydroxyethyl stearyl glycinate; Dihydroxyethyl tallowamine oxide; Dilaureth-4 dimonium chloride; Dilauryl acetyl dimonium chloride; Dilauryldimonium chloride; Dilinoleamidopropyl dimethylamine; Dimethicone copolyol; Dimethicone propyl PG-betaine; Dioctyldodecyl dodecanedioate;

Dipalmitoyl cystine; Dipalmitoyl hydroxyproline; Dipalmitoylethyl hydroxyethylmonium methosulfate; Dipalmoylethyl hydroxyethylmonium methosulfate; Distearoylethyl hydroxyethylmonium methosulfate; Distearyldimonium chloride; Ditallowamidoethyl hydroxypropylmonium methosulfate; Ditallowdimonium chloride; Ditallowethyl hydroxyethylmonium methosulfate; Ditallowoylethyl hydroxyethylmonium methosulfate; Ditridecyldimonium chloride; Ethyl ester of PVM/MA copolymer; Glyceryl distearate; Glyceryl lanolate; Glycine; Glycol oleate; Glycol ricinoleate; Guar hydroxypropyltrimonium chloride; Hexyl nicotinate; Histidine; Hyaluronic acid; Hydrogenated lanolin; Hydroxylated lanolin; Hydroxyproline; Hydroxypropyl biscetearyldimonium chloride; Hydroxypropyl bisisostearamidopropyldimonium chloride; Hydroxypropyl bisoleyldimonium chloride; Hydroxypropyl bisstearyldimonium chloride; Hydroxypropyl guar; Hydroxypropyl guar hydroxypropyltrimonium chloride; Hydroxypropyltrimonium amylopectin/glycerin crosspolymer; Hydroxypropyltrimonium gelatin; Hydroxystearyl methylglucamine; Inositol; Isobutylated lanolin oil; Isodecyl isononanoate; Isodecyl salicylate; Isoleucine; Isoleucine; Isononamidopropyl ethyldimonium ethosulfate; Isononyl isononanoate; Isopropyl ester of PVM/MA copolymer; Isopropyl lanolate; Isopropyl palmitate; Isostearamide DEA; Isostearamide MEA; Isostearyl diglyceryl succinate; Lactoyl methylsilanol elastinate; Lanolin; Lanolin; Lanolin alcohol; Lanolin cera; Lanolin linoleate; Lanolin ricinoleate; Lanosterol; Lapyrium chloride; Laurdimonium hydroxypropyl hydrolyzed soy protein; Lauroyl collagen amino acids; Lauroyl sarcosine Lauryl aminopropylglycine; Lauryl betaine; Lauryl diethylenediaminoglycine; Lauryl dimethylamine cyclocarboxypropyloleate; Lauryl glycol; Lauryl methyl gluceth-10 hydroxypropyldimonium chloride; Lauryl myristate; Lauryl palmitate; Lauryl sultaine; Linoleamidopropyl dimethylamine dimer dilinoleate; Linoleamidopropyl dimethylamine lactate; Linoleamidopropyl ethyldimonium ethosulfate; Lysine; Lysine PCA; Methacryloyl ethyl betaine/acrylates copolymer; Methicone; Methionine; Methyl aspartic acid; Methyl glutamic acid; Methyl hydroxycetyl glucaminium lactate; Methyl hydroxymethyl oleyl oxazoline; Methylbenzethonium chloride; Methylsilanol acetylmethionate; Methylsilanol acetyltyrosine; Methylsilanol elastinate; Methylsilanol hydroxyproline; Methylsilanol hydroxyproline aspartate; Minkamidopropalkonium chloride; Minkamidopropyl dimethylamine; Minkamidopropyl ethyldimonium ethosulfate; Monosaccharide lactate condensate; Myristoyl sarcosine; Myristyl hydroxyethyl imidazoline; Niacin; Norvaline; Octylacrylamide/acrylates/butylaminoethyl methacrylate copolymer; Octyldecyl trimonium chloride; Octyldodecyltrimonium chloride; Oleamidopropyl dimethylamine glycolate; Oleamidopropyl dimethylamine hydrolyzed collagen; Oleamidopropyl dimethylamine lactate; Oleamidopropyl dimethylamine propionate; Oleamidopropyl ethyldimonium ethosulfate; Oleoyl sarcosine; Oleyl betaine; Oleyl hydroxyethyl imidazoline; Oleyl lanolate; Olivamidopropyl dimethylamine; Olivamidopropyl dimethylamine lactate; Ouricury wax; Palm kernelamidopropyl betaine; Palmamidopropyl betaine; Palmitamidopropyl dimethylamine propionate; Panthenol; Panthenyl ethyl ether; Panthenyl ethyl ether acetate; Panthenyl hydroxypropyl steardimonium chloride; Panthenyl triacetate; Pantothenic acid polypeptide; Paraffinum liquidum; PCA ethyl cocoyl arginate; Petrolatum; PG-hydroxyethylcellulose cocodimonium chloride; PG-hydroxyethylcellulose lauryldimonium chloride; PG-hydroxyethylcellulose stearyldimonium chloride; Phenyl trimethicone; Phenylalanine; Phenylalanine; Phosphatidylcholine; Phthalic anhydride/glycerin/glycidyl decanoate copolymer; Polyacrylamide; Polybutylene terephthalate; Polyethylacrylate; Polyethylene; Polymethacrylamidopropyltrimonium chloride; Polyquaternium-11; Polysilicone-7; Polyvinyl acetate; Polyvinyl butyral; Polyvinyl imidazolinium acetate; Polyvinyl methyl ether; PVM/MA copolymer; PVP; PVP/dimethylaminoethylmethacrylate copolymer; PVP/eicosene copolymer; PVP/hexadecene copolymer; PVP/VA/itaconic acid copolymer; PVP/VA/vinyl propionate copolymer; PVP/VA copolymer; Pyridoxine; Pyridoxine dicaprylate; Pyridoxine dilaurate; Pyridoxine dioctenoate; Quaternium-70; Ricinoleamidopropyl ethyldimonium ethosulfate; Ricinoleamidopropyltrimonium chloride; Ricinoleamidopropyltrimonium methosulfate; Saffloweramidopropyl ethyldimonium ethosulfate; Serine; Silicone quaternium-1; Silicone quaternium-2; Silicone quaternium-3; Silicone quaternium-4; Silicone quaternium-5; Silicone quaternium-6; Silicone quaternium-7; Silicone quaternium-8; Silicone quaternium-9; Soyaethyl morpholinium ethosulfate; Soyamidopropyl ethyldimonium ethosulfate; Soyethyldimonium ethosulfate; Squalene; Starch diethylaminoethyl ether; Stearamidoethyl diethylamine; Stearamidoethyl ethanolamine; Stearamidoethyl ethanolamine phosphate; Stearamidopropyl cetearyl dimonium tosylate; Stearamidopropyl dimethylamine; Stearamidopropyl dimethylamine lactate; Stearamidopropyl ethyldimonium ethosulfate; Stearamidopropyl morpholine; Stearamidopropyl morpholine lactate; Stearamidopropyl trimonium methosulfate; Stearoyl sarcosine; Stearyl hydroxyethyl imidazoline; Stearyl octyldimonium methosulfate; Stearylvinyl ether/MA copolymer; Sucrose cocoate; Synthetic wax; Tall oil hydroxyethyl imidazoline; Threonine; Tricetylmonium chloride; Tridecyl salicylate; Trilaurylamine; Trimethylsilylamodimethicone; Trioctanoin; Tripaba panthenol; Triundecanoin; Tryptophan; Tyrosine; Undecylenyl alcohol; Urea; VA/crotonates/vinyl neodecanoate copolymer; VA/crotonates copolymer; Valine; Wheat germamidopropylamine oxide; Wheatgermamidopropyl ethyldimonium ethosulfate; *Zea mays*; and mixtures thereof.

In some embodiments, one or more fragrances are added to the nonaqueous hair styling composition to provide a scent to the hair styling composition. Any fragrance known in the art which imparts the desired scent to the hair styling composition may be used in embodiments of the invention. The fragrance that is selected for use in the hair styling composition can be used either alone or in combination in varying proportions with other fragrances.

In addition to the aforementioned compounds, other ingredients which may be used in the nonaqueous hair styling composition in accordance with embodiments of the invention are disclosed in the following U.S. Pat. Nos. 6,103,223; 6,093,384; 6,040,282; 6,024,948; 6,017,860; 6,001,339; 5,985,256; 5,976,517; 5,935,560; 5,810,023; 5,756,106; 5,723,113; 5,709,850; 5,681,546; 5,679,328; 5,658,558; 5,656,265; 5,565,193; 5,523,079; 5,419,896; 5,391,368; 5,277,899; 5,256,407; 5,120,532; 5,120,531; 5,104,642; 5,094,838; 5,049,377; 5,048,307; 5,032,391; 4,897,262; 4,840,790; 4,834,968; 4,764,363; 4,658,839; and 4,015,612. All of the preceding patents are incorporated by reference herein in their entirety for all purposes.

The nonaqueous hair styling composition in accordance with embodiments of the invention can be made by mixing Dipropylene glycol, Vinyl caprolactam/PVP/dimethylaminoethylmethacrylate copolymer and one or more of the additional nonaqueous additives. The hair styling composition can be applied to human hair or animal hair. Preferably, it is used to style human hair. A desired shape or configuration of the hair can be achieved by manually applying the hair styling composition to all or a portion of the hair, either wet or dry. Then the hair is combed or styled as desired. The hair is optionally subjected to heat from any heat source which is suitable for application to hair. With all formulations, the hair styling composition allows combing and/or styling during or after it is applied to the hair.

The following examples are given to exemplify embodiments of the invention. All numerical numbers are approximate. Variations from these numbers are within the scope of the invention. These examples should not be construed to limit the invention as otherwise described and claimed herein.

EXAMPLE 1

A nonaqueous hair styling laminator was obtained according to the compositions of TABLE II below. The amount of each component added to the nonaqueous hair style laminator is provided in TABLE II in approximate weight percent of the total composition

TABLE II

HAIR STYLING LAMINATOR

| Ingredient (INCI Name) | Range |
| --- | --- |
| Dipropylene Glycol | 42–60 |
| Trimethylpentanediol/Adipic Acid/Glycerin Crosspolymer | 0.5–3 |
| Glycereth-7-diglycerol-PEG-15 Cocamine/IPDI Copolymer | 1–5 |
| Denatured Alcohol | 10–40 |
| Vinyl caprolactam/PVP/dimethylaminoethyl methacrylate copolymer | 3–10 |
| Total | 100 |

The exemplary hair styling laminator obtained according to the composition of TABLE II was evaluated by a licensed cosmetologist on twenty four female test subjects covering practically all major hair textures, types, lengths and colors. It was found that the hair styling laminator can be used to style hair when applied to either wet or dry hair. For fine hair models where a straight, sleek, weighted texture was desired it was best to apply the hair styling laminator to damp hair by manually raking it through the hair, followed by drying the hair into the desired style. If necessary, an additional portion of the styling laminator was reapplied to the already dry, styled hair and briefly blow drying again to create a glossy, "wet-look" sheen on the hair. For thick, wavy, frizz-prone hair, where a sleek, straight, glossy-look was also desired, the best results were achieved by drying the hair into the desired style, generously applying the hair styling laminator to the dry hair by manually raking it through the hair, and briefly blow drying to leave a glossy, "wet-look" sheen on the hair. For fine or thick hair which has a "natural" wave or curl in which that wave or curl pattern was still desired after drying, the hair styling laminator was applied to damp hair and allowed to dry either naturally or with heat.

Overall, the exemplary hair styling laminator composition imparted a significant increase in manageability, hold and body (style support) to dried hair without brittleness. The resulting hair exhibited notably increased weight, shine and visual smoothness. There was a total elimination of static charge, flyaway and frizz. No flaking was observed with time or mechanical manipulation of the hair. The hair retained its shape and frizz control even when exposed to high humidity conditions. The treated hair was dry combed or brushed without degrading or breaking down the polymer coating, thereby retaining its weight and body after severe mechanical manipulation. The hair swings freely in all directions yet returns or falls back to its imparted shape without effort (similar to a beaded curtain). On selective models, the exemplary hair styling laminator was applied each time the hair was washed and styled for a minimum of 14 treatments over the course of two weeks and did not appear to have any drying effect on hair and actually appeared to leave the hair in better condition with less dryness than prior to starting treatments. In all cases, hair felt nominally coated but not excessive coated, sticky, greasy or tacky.

Exemplary Method of Preparation

Dipropylene glycol was charged into a dry, stainless steel tank equipped with a propeller type mixer and was stirred at a moderate rate. Trimethylpentanediol/adipic acid/glycerin crosspolymer was slowly added by weight difference. The mixture of Dipropylene glycol and Trimethylpentanediol/adipic acid/glycerin crosspolymer was stirred until the solution was clear and lumps were not visible. Glycereth-7-diglycerol-PEG-15 cocamine/IPDI copolymer was slowly added by weight difference. The mixture of Dipropylene glycol, Trimethylpentanediol/adipic acid/glycerin crosspolymer, and Glycereth-7-diglycerol-PEG-15 cocamine/IPDI copolymer was stirred until a clear, homogenous solution was obtained. Denatured alcohol was added to the mixture and stirred until a clear, homogenous solution was obtained. Vinyl caprolactam/PVP/dimethylaminoethyl methacrylate copolymer was slowly added by weight difference to the mixture of Dipropylene glycol, Trimethylpentanediol/adipic acid/glycerin crosspolymer, Glycereth-7-diglycerol-PEG-15 cocamine/IPDI copolymer, and denatured alcohol. The resulting mixture was stirred until a clear, homogenous solution was obtained. All mixing was conducted at room temperature.

The exemplary hair styling composition of TABLE III was sampled at the top and the bottom and was tested for odor, color, specific gravity, refractive index, standard plate count, and gram negative bacteria, the results of which are presented below in Table III. The specific gravity was measured using a pycnometer.

TABLE III

| Test | Result |
| --- | --- |
| Appearance | Clear, slightly viscous liquid |
| Color | Water white |
| Odor | Slight alcohol |
| Specific Gravity @ 25° C. | 0.949–0.959 |
| Refractive Index | 1.42–1.43 |
| Standard Plate Count | <10 CFU/gram |
| Gram Negative Bacteria | Negative |

EXAMPLE 2

Hair Styling Serum

An exemplary hair styling serum was prepared according to the following procedure. The amount of each component added to the hair styling serum is provided in Table IV in weight percent of the total composition.

TABLE IV

HAIR STYLING SERUM

| Ingredient (INCI Name) | Range |
| --- | --- |
| Dipropylene Glycol | 82–95 |
| Trimethylpentanediol/ADIPIC Acid/Glycerin Crosspolymer | 0.5–3 |
| Glycereth-7-diglycerol-PEG-15 Cocamine/IPDI Copolymer | 1–5 |
| Vinyl caprolactam/PVP/dimethylaminoethyl methacrylate copolymer | 3.5–10 |
| Total | 100 |

The hair styling serum obtained according to the composition of TABLE IV was evaluated by a licensed cosmetologist on twelve female test subjects with thick, wavy, porous, frizz prone hair. It was found that the hair styling serum can be used to style hair when applied to either wet or dry hair. To achieve a sleek, straight, glossy-look with total elimination of Frizz, it was best to apply the hair styling serum to damp hair by manually raking it through the hair, followed by drying the hair to the desired straightness. An additional portion of the styling serum was reapplied to the already dry, straight hair and briefly blow dried again to leave a glossy, "wet-look" sheen on the hair. Overall, the hair styling serum exhibited all the benefits described above for the hair styling laminator of Example 1.

EXAMPLE 3

Hair Styling Lotions

Exemplary hair styling lotions A, B and C were prepared substantially according to the following TABLES V through VII and the following procedures:

TABLE V

HAIR STYLING LOTION A

| Ingredient (INCI Name) | Range |
| --- | --- |
| Denatured Alcohol (Anhydrous) | 20–40 |
| Benzophenone-3 | 0.2–0.5 |
| Pentylene Glycol | 5–10 |
| Propylene Glycol | 40–60 |
| Cetearyl Octanoate | 1–5 |
| Trimethyl pentanediol/Aipic acid/Glycerin crosspolymer | 1–3 |
| PVP/VA | 5–15 |
| Dimethicone/IPDI Copolymer | 1–5 |
| Total | 100 |

Procedure

Denatured Alcohol is charged into a dry, stainless steel tank equipped with a propeller type mixer. Add Benzophenone-3 and stir until dissolved. Add each subsequent ingredient individually and stir between each addition. A clear to slight hazy lotion resulted.

TABLE VI

HAIR STYLING LOTION B

| Ingredient (INCI Name) | Range |
| --- | --- |
| Denatured Alcohol (Anhydrous) | 20–40 |
| Dipropylene Glycol | 40–60 |
| Cyclomethicone | 10–20 |
| Isostearyl Palmitate | 2–6 |
| Glycereth-7-diglycerol-PEG-15 Cocamine/IPDI Copolymer | 1–5 |
| Vinyl caprolactam/PVP/Dimethylaminoethyl methacrylate copolymer | 3–10 |
| Adipic acid/Diethylene glycol/Glycerin crosspolymer | 0.5–3 |
| Total | 100 |

Procedure

Denatured alcohol is charged into a dry, stainless steel tank equipped with a propeller type mixer. Each ingredient was individually added with stirring between each addition. A clear to slightly hazy lotion resulted.

TABLE VII

HAIR STYLING LOTION C

| Ingredient (INCI Name) | Range |
| --- | --- |
| Denatured Alcohol (ANHYDROUS) | 20–40 |
| Acrylate Copolymer | 0.5–3 |
| Dipropylene Glycol | 40–75 |
| Vinyl caprolactam/PVP/Dimethylaminoethyl methacrylate copolymer | 0.5–3 |
| Adipic Acid/Diethylene Glycol/Glycerin Crosspolymer | 1–3 |
| Ethyl hexyl Methoxycinnamate | 0.2–1.0 |
| DI-PEG-2 Soy Amine/IPDI copolymer | 1–5 |
| Total | 100 |

Method of Preparation

In an appropriate size vessel equipped with a variable speed mixer add the denatured alcohol. With high shear stirring add the acrylate copolymer. Stir until a clear, homogeneous dispersion results. To the batch add Dipropylene glycol, vinyl copolymer and the remaining elements one at a time and stirring between each addition until a clear homogeneous solution results.

As demonstrated above, embodiments of the invention provide a nonaqueous hair styling composition and a method of making and using the composition. The hair styling composition may provide one or more of the following advantages. For example, the hair styling composition can be used on both dry hair and wet hair. The Style can be held until next shampoo. It provides a moisture barrier which protects the style from reverting to natural shape in high humidity conditions. An exemplary hair styling composition may further be easily removed with detergent and water. It further may remove frizz from dry hair, and can be used anytime. The nonaqueous hair styling composition imparts hold, shine, manageability, body, weight, frizz control, conditioning and moisturization to the hair without making the hair unmanageably stiff, brittle, sticky, greasy, tacky, soft or appear excessively coated. The nonaqueous hair styling composition can be combed or brushed without or with limited loss of hold or without the possibility of flaking.

While the invention has been described with a number of embodiments, the scope of the invention is not intended to be limited by the specific embodiments. Modifications and variations from the described embodiments exist. Although numerous ingredients suitable for formulating the hair styling composition have been listed, the list is by no means exhaustive. Other unlisted ingredients, both known and unknown, may also be used in embodiments of the invention. While the hair styling composition is a hair care product, the same composition may also be used as a skin care product which is applied to a portion of a skin, both human and animal. Skin care products may be made by modifying the hair styling compositions described herein. The appended claims intend to cover all such modification and variations as falling within the scope of the invention.

What is claimed is:

1. A hair styling composition comprising: at least one vinyl compolymer, at least one nonaqueous solvent therefore, at least one urethane copolymer, at least one polyester, and at least one additional nonaqueous solvent therefore, wherein said urethane copolymer is glycereth-7-diglycerol-polyethyleneglycol-15 cocamine/isophorone diisocyanate.

2. A hair styling composition comprising: at least one vinyl copolymer, at least one nonaqueous solvent therefore, at least one urethane copolymer, at least one polyester, and at least one additional nonaqueous solvent therefore, wherein said polyester is selected from the group consisting of adipic acid/diethylene glycol/glycerin crosspolymer, tripentanediol/adipic acid glycerin crosspolymer, tripentanediol/adipic acid/isononanoic acid crosspolymer, tripentanediol/adipic acid copolymer, and mixtures thereof.

3. A hair styling composition comprising: at least one vinyl copolymer, at least one nonaqueous solvent therefore, at least one urethane copolymer, at least one polyester, and at least one additional nonaqueous solvent therefore, wherein said polyester is trimethylpentanediol/adipic acid/glycerin crosspolymer.

4. A hair styling laminator comprising the following components present within the listed ranges by weight percent:

| Ingredient (INCI Name) | Range |
| --- | --- |
| Dipropylene Glycol | 42–60 |
| Trimethylpentanediol/Adipic Acid/Glycerin Crosspolymer | 0.5–3 |
| Glycereth-7-diglycerol-PEG-15 Cocamine/IPDI Copolymer | 1–5 |
| Denatured Alcohol | 10–40 |
| Vinyl caprolactam/PVP/Dimethylaminoethyl methacrylate copolymer. | 3–10 |

5. A hair styling serum comprising the following components present within the listed ranges by weight percent:

| Ingredient (INCI Name) | Range |
| --- | --- |
| Dipropylene Glycol | 82–95 |
| Trimethylpentanediol/Adipic Acid/Glycerin Crosspolymer | 0.5–3 |
| Glycereth-7-diglycerol-PEG-15 Cocamine/IPDI Copolymer | 1–5 |
| Vinyl caprolactam/PVP/Dimethylaminoethyl methacrylate copolymer. | 3.5–10 |

6. A hair styling lotion comprising the following components present within the listed ranges by weight percent:

| Ingredient (INCI Name) | Range |
| --- | --- |
| Denatured Alcohol (Anhydrous) | 20–40 |
| Benzophenone-3 | 0.2–0.5 |
| Pentylene Glycol | 5–10 |
| Propylene Glycol | 40–60 |
| Cetearyl Octanoate | 1–5 |
| Trimethyl pentanediol/Adipic acid/Glycerin crosspolymer | 1–3 |
| PVP/VA | 5–15 |
| Dimethicone/IPDI Copolymer | 1–5. |

7. A hair styling lotion comprising the following components present within the listed ranges by weight percent:

| Ingredient (INCI Name) | Range |
| --- | --- |
| Denatured Alcohol (Anhydrous) | 20–40 |
| Dipropylene Glycol | 40–60 |
| Cyclomethicone | 10–20 |
| Isostearyl Palmitate | 2–6 |
| Glycereth-7-diglycerol-PEG-15 Cocamine/IPDI Copolymer | 1–5 |
| Vinyl caprolactam/PVP/Dimethylaminoethyl methacrylate copolymer | 3–10 |
| Adipic acid/Diethylene glycol/Glycerin crosspolymer | 0.5–3 |
| Total | 100. |

8. A hair styling lotion comprising the following components present within the listed ranges by weight percent:

| Ingredient (INCI Name) | Range |
| --- | --- |
| Denatured Alcohol Anhydrous | 20–40 |
| Acrylate Copolymer | 0.5–3 |
| Dipropylene Glycol | 40–75 |
| Vinyl caprolactam/PVP/Dimethylaminoethyl methacrylate copolymer | 0.5–3 |
| Adipic acid/Diethylene Glycol/Glycerin Crosspolymer | 1–3 |
| Ethyl hexyl Methoxycinnamate | 0.2–1.0 |
| DI-PEG-2 Soy Amine/IPDI copolymer | 1–5. |

* * * * *